United States Patent [19] [11] 4,200,097
Hobbs, Jr. et al. [45] Apr. 29, 1980

[54] DISPOSABLE DOUCHE

[75] Inventors: Thomas G. Hobbs, Jr.; Eugene A. Stephens, both of Lynchburg, Va.

[73] Assignee: C. B. Fleet Company Incorporated, Lynchburg, Va.

[21] Appl. No.: 931,241

[22] Filed: Aug. 4, 1978

[51] Int. Cl.² .................... A61M 7/02; A61M 1/00
[52] U.S. Cl. .................................. 128/251; 128/232; 128/274
[58] Field of Search ............... 128/230–232, 128/251, 274, 272; 222/92, 96, 206; 401/133; 137/522; 251/82

[56] References Cited
U.S. PATENT DOCUMENTS 3,157,323  11/1964  Kitterman ........................ 222/212
3,401,695   9/1968  Rosenberg et al. ............... 128/232

FOREIGN PATENT DOCUMENTS 2603279  8/1977  Fed. Rep. of Germany .......... 128/251

Primary Examiner—Robert W. Michell
Assistant Examiner—Thomas Wallen
Attorney, Agent, or Firm—Mason, Fenwick & Lawrence

[57] ABSTRACT

A disposable douche for dispensing fluids contained therein including a collapsible container, a sealing closure, a nozzle assembly having a passageway communicating with the interior of the container for dispensing the contents of the container, a portion of the nozzle being retractable into the interior of the container to a storage position and being extendable to a use position, seals between the nozzle and the closure and between the closure and the container for preventing leakage from the container, a sleeve valve mounted on the nozzle for controlling the flow of fluids from the container through the nozzle, abutments on the closure and sleeve valve for opening the sleeve valve when the nozzle is extended from the retracted to the use position.

19 Claims, 6 Drawing Figures

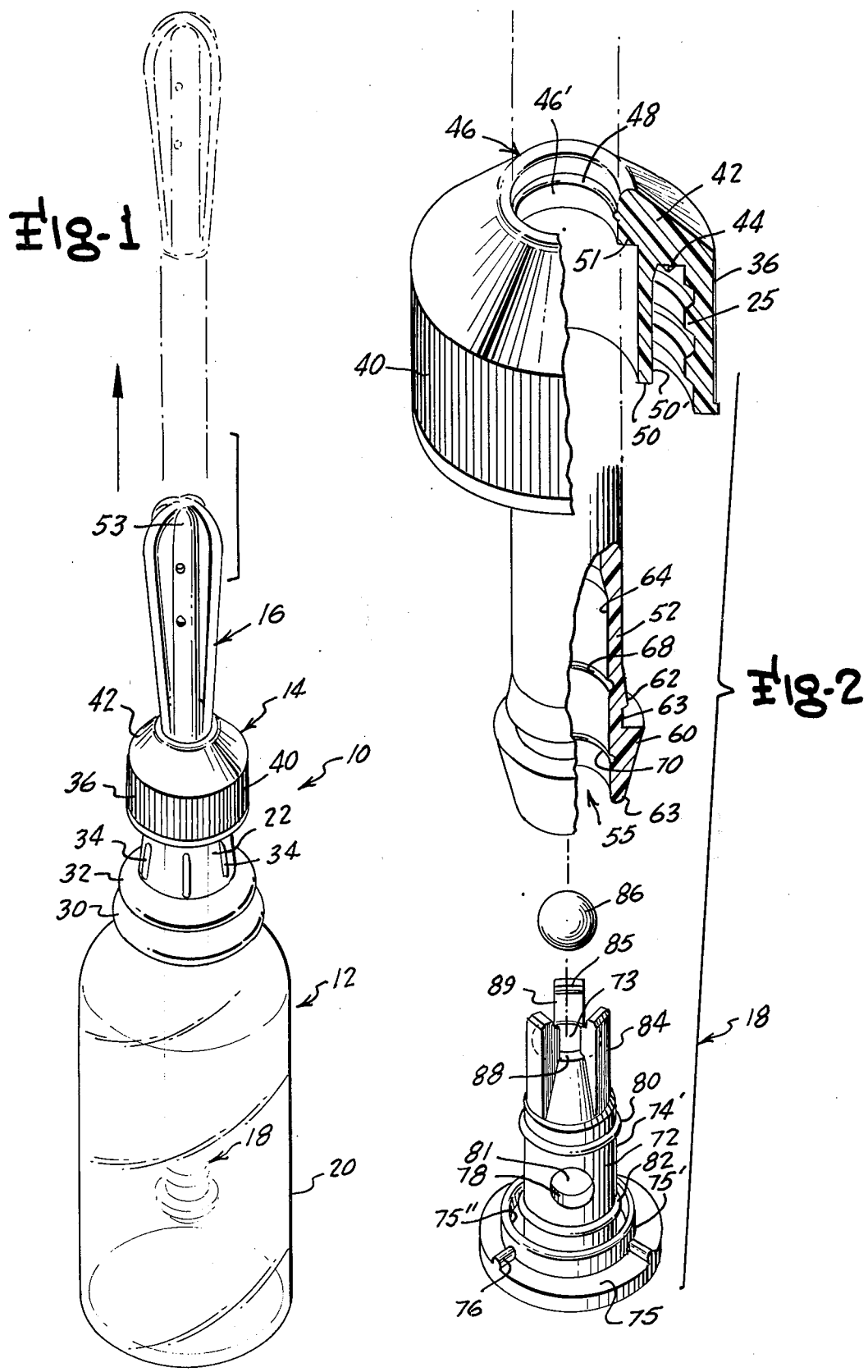

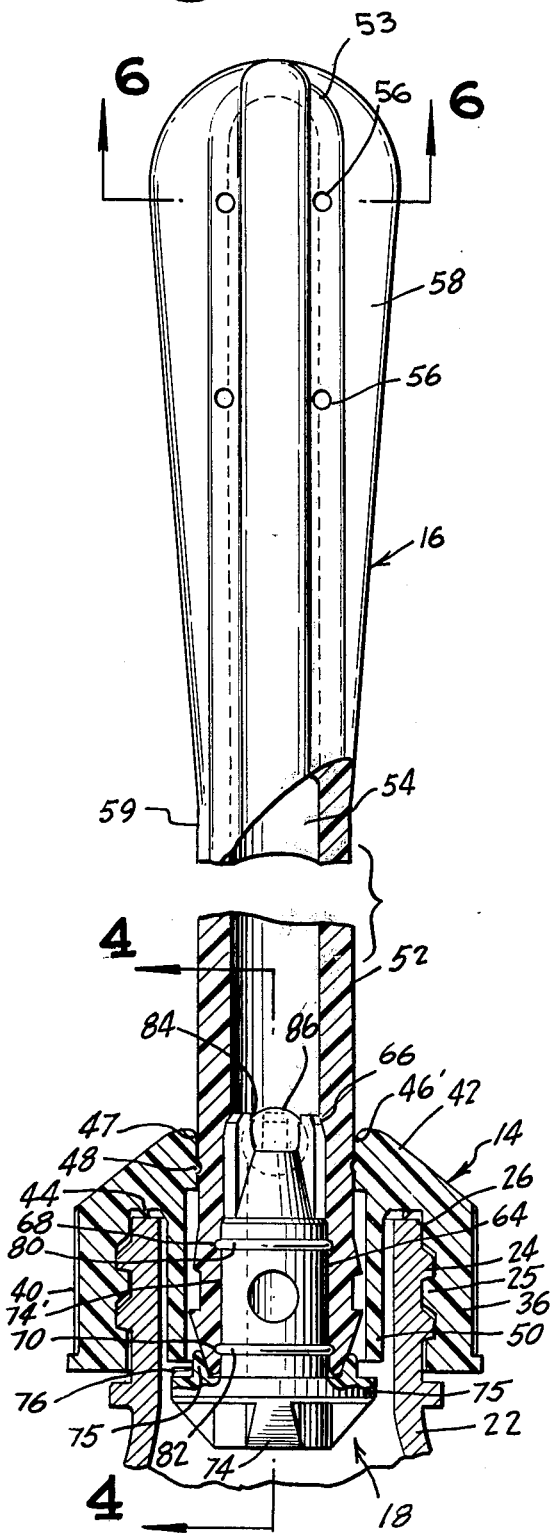
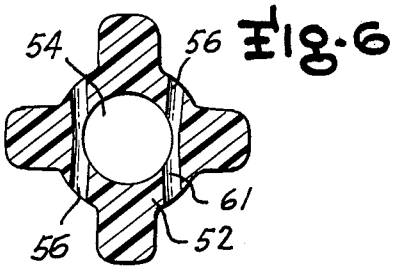
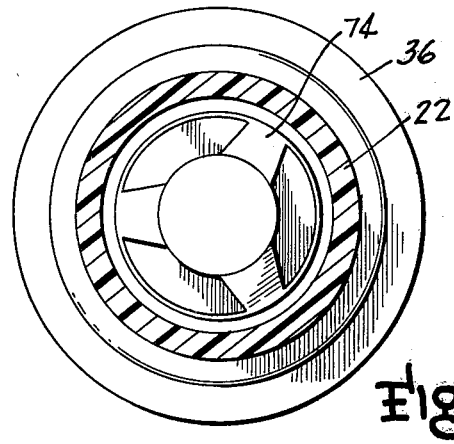
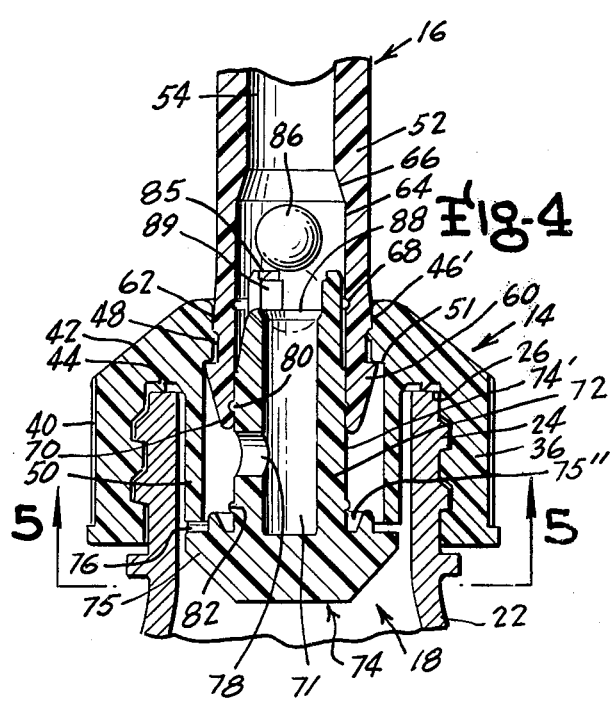

DISPOSABLE DOUCHE

This invention is in the field of dispensing devices and is more specifically directed to a disposable douche having a telescoping elongated nozzle which is retractable into a container to supply a desired cleansing solution through the nozzle after the nozzle has been extended. A valving assembly prevents any accidental leakage of the solution during shipment and prevents any leakage from the nozzle after it is extended until pressure is applied to the container to dispel the solution.

Previously known douches have usually been of the refillable type which require the mixing of proper quantities of powders or liquids to form the desired solution. These individually mixed solutions have been of varying concentration because of the human factor involved in measuring and mixing. Improper measuring or mixing of the douche composition results in either ineffective weak solutions or strong solutions which may cause inflammation or permanent damage to the tissues of the vaginal wall.

Utilizing premixed solutions permits accurate control of the concentration of constituents in the solution; however, it incurs the possibility of contamination of the douche during the addition of the solution because of the necessity of exposing the solution and the device to handling and to the atmosphere. These previously known reusable devices have frequently been unsanitary due to the lack of proper cleaning after successive uses resulting in the introduction of infectious bacteria into the vagina. This risk of infection is directly related to the cleanliness with which the device is maintained.

Previously known reusable douches have been particularly inconvenient for the user when away from home due to the necessity of carrying the equipment and appropriate ingredients for mixing the solution and for maintaining cleanliness of the device due to the frequent lack of facilities necessary to perform these operations.

Disposable douches have previously been available; however, these devices have usually been bulky and inconvenient to pack and carry and have been inconvenient to use because it has been necessary to assemble various components together to provide an operable device. Additionally, these previously known devices have been susceptible to leakage both in transit and prior to use.

Therefore, it is the primary object of the present invention to provide a new and improved disposable douche.

An additional object of the present invention is to provide a one-piece disposable douche with a pullup nozzle which eliminates any assembly of parts by the user thereby requiring only the pulling up of the nozzle to place the device in condition for use.

Another object of the present invention is to provide a disposable douche having valves which prevent leakage while the douche is being transported and prevent leakage through the nozzle after it has been extended and while it is being placed in position.

A further object of the present invention is to provide a disposable douche having a flexible bellows type neck on the solution container with the remaining component parts being formed of a soft flexible material thereby permitting the user to adjust the nozzle to the most comfortable position without discomfort or injury.

A still further object of the present invention is to provide a disposable douche in which the douching solution is premixed and premeasured and the device is preassembled and completely disposable thereby eliminating the mixing, measuring or storing of bulky bags and syringes.

Another object of the present invention is to provide a disposable douche which is safe, sanitary, effective and ready to use.

A still further object of the present invention is to provide a disposable douche which is compact and easily transported for shipment to the user and/or for transport by the user.

A better understanding of the preferred embodiment of the subject invention will be enabled when the following written description is considered in conjunction with the appended drawings in which:

FIG. 1 is a perspective view of the preferred embodiment including a partly broken away phantom view of the disposable dispensing device of the present invention in the extended position;

FIG. 2 is an exploded and enlarged fragmentary perspective view of the cap, nozzle and valve assembly of the present invention;

FIG. 3 is a fragmentary sectional view of the nozzle in a partially extended condition before opening of the valve assembly;

FIG. 4 is a partial sectional view taken along lines 4—4 in FIG. 3 but with the nozzle fully extended and the valve assembly opened;

FIG. 5 is a sectional view taken along lines 5—5 of FIG. 4; and

FIG. 6 is a sectional view taken along lines 6—6 of FIG. 3.

Attention is initially invited to FIGS. 1 and 2 of the drawings in which is illustrated the preferred embodiment of the invention, generally designated 10, which includes a container 12, a cap or closure assembly 14, a nozzle 16 and a valve assembly 18.

The solution to be supplied from the douche is retained in container 12 which is in the general form of a very thin flexible wall plastic bottle having an enlarged portion 20 for retaining approximately 4½ fluid ounces of cleansing fluid. This container volume might be varied if desired. The thin flexible wall permits the container to be simply and easily collapsed by the user when the user grasps the container in one hand and presses inwardly with the fingers and palm of the hand to apply pressure to the fluid and expel the fluid from the container through the nozzle 16. The container 12 has a thick walled open-ended neck portion 22 at the upper end thereof with male buttress threads 24 extending around the upper end of the neck portion.

The cap or closure 14, as shown in FIGS. 3 and 4, has similar inwardly directed female buttress threads 25 to engage the threads 24 on the neck portion 22. The upper end of the neck portion 22 has a flat sealing surface 26 adjacent to the opening therethrough to permit the creation of a fluid tight seal between the cap or closure 14 and the container 12.

A flexible bellows section 28 connects the enlarged reservoir portion 20 with the thick walled neck portion 22 and includes two convolutions 30 and 32 being formed of the conventional bellows configuration. The bellows section greatly increases the angular freedom of movement between the nozzle 16 and the reservoir 20, thereby permitting the user to adjust the angular orientation between the nozzle 16 and the reservoir 20 to the most comfortable position for insertion and use. The neck portion 22 includes lugs 34 in the form of outwardly projecting ribs, as shown in FIG. 1, to provide a positive locking of the bottle in the automatic capping equipment to insure sufficient torque to provide a positive seal of the cap or closure on the bottle.

The cap or closure 14, moulded of a relatively stiff plastic material such as low density polyethylene, includes a generally cylindrical outer portion 36 having the female buttress threads 25 on the inner surface thereof, as shown in FIGS. 2, 3 and 4. As noted earlier, the female buttress threads 25 on the cap 14 engage the male buttress threads 24 on the neck portion 22 of the container 12 to retain the cap in the desired assembled position. On the outer surface of the cylindrical portion 36 of the cap are vertically arranged serrations 40 to provide a positive grip in the chucks of the automatic capping equipment to insure a positive seal of the device while being assembled for shipment to the consumer. Extending upwardly and inwardly from the top of the cylindrical portion 36 of the cap 14 is a contiguous conical portion 42 having a downward projecting circumferential sealing ridge 44 of triangular cross-section or other suitable shape positioned to engage the flat sealing surface 26 of the neck portion 22, as shown in FIGS. 3 and 4.

Extending through the center of the conical section 42 of the cap is a round nozzle opening 46 formed by a surrounding surface 46' of the cap with the opening having an inside diameter which is approximately the same diameter as a portion of the outer surface of the nozzle 16, as shown in FIGS. 3 and 4. The upper edge of the conical portion 42 has a radius 47 adjacent the opening 46 to permit the nozzle to enter the cap easily in the initial assembly operation.

An inwardly directed sealing bead wiper 48 is circumferentially formed on the surface 46' forming the opening 46 and is of approximately semi-circular cross-section. The sealing bead wiper is formed with an inside diameter which is slightly smaller than the outside diameter of the nozzle 16 passing therethrough. The bead wiper acts as a compression ring indenting into the nozzle to form a seal between the cap 14 and the nozzle 16. When the nozzle is extended, this sealing bead and wiper wipes fluid from the outer surface of the nozzle as it passes the bead. The bead wiper 48 also functions as a seal to prevent the escape of any solution from the interior of the container around the extension nozzle except for the desired flow of solution through the interior of the nozzle.

An axially projecting cylindrical abutment skirt 50 projects downwardly from an inner surface of the conical portion 42 of the cap 14 and has an outer surface 50' with outside diameter which is less than the inside diameter of the inner surface of the neck portion 22 of the container. The abutment skirt 50 has an inner surface 50'' with inside diameter which is larger than the outside diameter of the outer surface of the nozzle 16. An abutment shoulder 51 extends radially inwardly from the inner surface 50'' of the abutment skirt 50 to the surface 46' forming the opening 46 in the cap 14. Actuation of the valve assembly 18 is caused by the abutment skirt 50 when the nozzle is extended as indicated by FIG. 4 and as explained in detail hereinafter.

As can be seen from the drawings, the nozzle 16 includes a generally hollow cylindrical body 52 having a closed upper end 53 thereof, a flow passageway 54 extending along the center of the nozzle body 52 and an open lower end 55. The nozzle may be formed of a relatively soft material such as ethylene vinyl acetate; however, other plastic materials could be used if desired. Four pairs of outlet orifices 56 are circumferentially spaced apart at equal distances on the upper portion of the nozzle body 52 with each pair of orifices spaced from the closed end 53 of the nozzle body. The orifices 56 communicate with the flow passageway 54 and fluid solution from the container 12 is forced through the orifices 56 to produce the desired flushing action. Adjacent orifices are formed (or connected) by a single orifice passageway 61 extending through the nozzle body 52 and intersecting the flow passageway 54, as shown in FIG. 6. This configuration simplifies the molding of the nozzle by permitting core pins to come in from both sides and abut at the center.

Spaced between the orifices 56 is a plurality of longitudinal ribs 58 extending radially outwardly from the body 52. These ribs are generally semi-circular in axial cross-section at the closed end 53 of the nozzle body 52. The ribs taper radially inward toward the open end 55 of the nozzle body 52 to merge with the cylindrical shape of the nozzle body 52 below the outlet orifices, as shown at 59. The number, size and shape of the ribs 58 may be varied as desired and the outlet orifices 56 may be of any desired diameter and location to achieve desired flow characteristics. This configuration forms flow passageways between the ribs to create a uniform and effective cleansing action by the douche solution after it flows through the outlet orifices 56.

The nozzle body 52 has a flange shoulder 60 at the lower end thereof to seat against the abutment shoulder 51 on the cap 14, as shown in FIG. 4, to prevent extraction of the nozzle beyond the desired extended position. A circumferential retaining ridge 62 extends outwardly from the nozzle body 52, as best shown in FIG. 2, and is spaced apart a short distance from the flange shoulder 60 to form a slot 63 therebetween. This ridge 62 seats against the wiper bead 48 when the nozzle is fully extended, as shown in FIG. 4, thereby locking the nozzle in the extended position. The retaining ridge 62 is tapered outwardly toward the open end 55 of the nozzle body to permit the wiper bead 48 to ride up the retaining ridge and drop into the slot 63. The flange shoulder 60 is tapered toward the open end 55 of the nozzle body 52 to an outside diameter which is smaller than the inside diameter of the wiper bead 48 to permit insertion of the nozzle into the cap 14 without requiring excessive force and without causing damage to the wiper bead 48.

The portion of the nozzle passageway 54 adjacent the open end 55 has an enlarged inside diameter portion 64 extending inwardly from the open end 55 of the nozzle body 52 with a short tapered section 66 connecting the larger inside diameter portion 64 to the flow passageway 54 as best shown in FIG. 4. Two optional circumferential locking grooves 68 and 70 are spaced apart in the surface of the enlarged portion 64, as best shown in FIG. 2.

The flow of fluid from the container 12 through the nozzle 16 is controlled by the valve assembly 18 as shown in FIGS. 2, 3 and 4. The valve assembly 18 includes a valve body 72 which is of hollow cylindrical configuration with a flow passageway 71, an open upper end 73, and a closed lower end 74. The diameter of the outer surface 74' of an upper portion of the valve body 72 is slightly larger than the inside diameter of the enlarged bore 64 in the nozzle 16 thereby creating a snug fit between the nozzle body 52 and the upper portion of the valve body 72 when the valve body is inserted in the enlarged portion 64 of the nozzle passageway 54, as shown in FIG. 3 so the valve will not fall out of the nozzle in an open position.

The lower end 74 of the valve body 72 includes an outwardly extending abutment flange 75 which engages a lower edge of the abutment skirt 50 on the cap 14 to open the valve assembly, as shown in FIG. 4. Extending upwardly from the upper surface of the abutment skirt 50 is a protruding circular sealing ridge 75' which is concentric with the valve body 72. An outwardly and upwardly tapered sealing surface 75" provided on the sealing ridge 75' is dimensioned to squeeze or compress the lower tapered end of the nozzle flange shoulder 60 to form a leak-tight seal when the valve body 72 is in the closed position as shown in FIG. 3. The amount of compression and consequent sealing capability may be changed by appropriate changes in the inside surface of this sealing ridge and lower tapered end of the nozzle.

Raised pads 76 on top of the valve flange 75 provide an opening between the top of the valve flange 75 and the bottom of the cap skirt 50 as shown in FIG. 4. A valve port 78 extends radially into the flow passageway 71 of the valve body 72 to permit the solution passing through the openings under cap skirt 50 to flow into the flow passageway 71 of the valve body 72 when the valve assembly is in the position shown in FIG. 4. The outer surface of the upper portion of the valve body 72 may include two circumferential spaced apart locking and sealing beads 80 and 82 for engagement with the grooves 68 and 70 in the nozzle body 52 when the valve body is assembled as shown in FIG. 3. The locking bead 80 engages the lower groove 70 when the nozzle is fully extended and the valve body 72 has been moved partially out of the enlarged inside diameter portion 64 of the nozzle body 52, as shown in FIG. 4. Groove 68 and 70 may be eliminated in which case grooves will be formed by the sealing beads 80 and 82 indenting into the softer nozzle.

An alternative configuration to the valve body 72 with beads 80 and 82 would be to omit the beads and have the valve body formed with a slightly larger diameter than the inside diameter of the enlarged portion 64 of the nozzle flow passageway 54 thereby providing a snug fit tight seal between the valve body 72 and the nozzle body 52 when the valve assembly is in the positions shown in FIGS. 3 and 4.

Adjacent and spaced apart around the open end 73 of the valve body 72 are three axially extending ball valve fingers 84 which retain a ball valve 86 of corrosion resisting metal or plastic against a conical valve seating surface 88 adjacent the open end 73 of the valve body 72. The tapered surface 66 in the nozzle body 52 squeezes the ends of the fingers 84 together around the ball to produce a permanent set in the fingers 84 to retain the valve ball 86 against valve seat 88 after the valve is opened when the nozzle has been fully extended. This also insures retention of the ball while handling the nozzle assemblies prior to installation on the containers.

The ball is in the position as shown in FIG. 3 prior to the extension of the nozzle. When the valve assembly 18 is open, as shown in FIG. 4, and pressure is applied by the user to the container, the valve ball 86 becomes unseated from the valve surface 88 due to the force of the so pressurized douche liquid, and escapes from the fingers.

The diameter formed by the inner surface 89 of valve fingers 84 is slightly less than the outside diameter of the ball 86 thereby causing the ball 86 to be lightly retained in the seated position of FIG. 3 until assembly. The valve fingers 84 extend above the point of contact between the ball and the fingers and are dimensioned to be pressed inwardly by the tapered section 66 of the nozzle body 52 about the upper portion of the ball 86 as also shown in FIG. 3 to provide positive retention of the ball after assembly.

The upper portions of the fingers 84 have cutouts 85 adjacent the inner surfaces thereof to permit the ball when forced away from the valve seat 88 only a short distance to be released into the nozzle passageway 54 when pressure is applied to the fluid solution within container 20. It will be noted that the ball 86 is of larger diameter than the orifices 56 and therefore will be retained in passageway 54 both during and after use. The valve seat 88 ensures a line contact between the ball 86 and the valve seat to provide a reasonably fluid tight seal prior to use to prevent leakage or dripping while handling and inserting the nozzle.

The retention of the ball against the valve seat prevents the fluid solution from dripping out of the orifices 56 when the bottle is inverted prior to the application of pressure to the fluid in the container 12. The pressure required to be applied to the container 20 to force the ball 86 away from the fingers 84 into the position as shown in FIG. 4 is minimal. The release of the ball opens valve passage 71 which greatly reduces the squeeze pressure required by the user to empty the container 12.

This disposable douche is normally shipped in the condition shown in FIG. 1 wherein the valve body 72 is fully inserted into the open end 55 of the nozzle body 52. The sealing beads 80 and 82, if used, will engage the grooves 68 and 70 if used in the nozzle body 52 and the ball valve 86 will be held against the valve seat 88 by the fingers 84 that are pressed against the tapered portion 66 of the nozzle body 52. The valve will be tightly sealed and held from falling out of the nozzle by the sealing ring compressing the end of the nozzle and friction between the larger valve body and the smaller inside diameter of the nozzle. At the time of assembly, the container 20 is filled with an appropriate fluid solution to accomplish the desired cleansing. The cap nozzle assembly 14, which is preassembled on separate equipment, is then threaded onto the neck portion 22 of the container 20 by the chuck of a capping machine by grasping the serrations 40 on the cap while the lugs 34 on the neck portion are held by movable clamps on the capper. The cap is tightened sufficiently by adjustable torque of the capper chucks to form a first leakproof seal between the sealing ridge 44 on the cap 14 and the sealing surface 26 at the upper end of the neck portion 22. A second leakproof seal is formed between the nozzle body 52 and the cap 14 by the wiper sealing bead 48 pressing against the outer surface of the nozzle body 52. A third leakproof seal is achieved between the valve body 72 and the nozzle body 52 as previously described.

The unit may be shipped to the user in a sealed plastic overwrap which is opened by tearing along the bottom or side seals of the wrapper. The overwrap may be used to grasp the nozzle ribs 58 to pull the nozzle 16 from the position shown in FIG. 1 outwardly through the position shown in FIG. 3 to the fully extended position shown in FIG. 4 to prevent finger contact. When the nozzle is fully extended, the wiper bead 49 drops into a position behind the retaining ridge 62 securing the nozzle in the extended position and the flange shoulder 60 on the nozzle body contacts the abutment shoulder 51 on the cap 14 as shown in FIG. 4. As the nozzle passes the position shown in FIG. 3, the abutment flange 75 contacts the abutment skirt 50 of the cap 14 to cause the valve body 72 to be moved downwardly relative to the nozzle body 52 to the position shown in FIG. 4. In this position, fluid solution from the container 20 flows under the abutment skirt 50 and into valve port 78 into the valve flow passageway 71 in the center of the valve body 52.

The nozzle is then inserted into the vagina a sufficient distance to achieve the desired internal cleansing and the container 20 is squeezed firmly by the user to force the valve ball 86 away from the valve seat 88, as shown in FIG. 4. Suitable pressure may then be applied to provide the desired flow rate of liquid until the container 20 is empty. The nozzle 16 may then be removed and pushed back into the container 12 to the position shown in FIG. 1 for easy disposal.

Numerous modifications of the subject invention will undoubtedly occur to those with skill in the art; however, it should be understood that the spirit and scope of the invention is to be limited solely in light of the appended claims.

I claim:

1. A disposable device for dispensing douche liquids and the like contained therein, said disposable device comprising a collapsible container having a quantity of liquid therein, a nozzle telescopically mounted on said container and having a passageway with an inner end communicating with the interior of said container for dispensing said liquid contents of said container, a portion of said nozzle being retractable into the interior of said container to a storage position and being extendable to a use position, a first valve means mounted in the inner end of said passageway of said nozzle internally of said container for controlling the flow of said liquid from said container into said passageway, means for opening said first valve means in response to movement of said nozzle to its use position from said storage position, and a second valve means mounted in said passageway for permitting the flow of said liquid through said passageway in response to the opening of said first valve means and the creation of a predetermined pressure on the said liquid contained in the container wherein said second valve means opens to permit the flow of liquid into and through said passageway.

2. The disposable device of claim 1 wherein said container includes a bellows portion to permit the nozzle to be moved relative to the container thereby permitting the user to orient the nozzle to the most convenient position relative to said container.

3. The disposable device of claim 1 wherein said first valve means includes a cylindrical sleeve valve body slidably mounted in said nozzle passageway and sized to sealingly engage the wall of said nozzle passageway, said sleeve valve body having a flow passageway therethrough communicating with the passageway in said nozzle and selectively communicable with the interior of said container, and wherein said means for opening said first valve means includes an abutment flange on said sleeve valve body and an abutment on said container for engaging said abutment flange on said sleeve valve body and moving said sleeve valve body in said nozzle passageway to cause said passageway in said sleeve valve body to communicate the interior of said container with said nozzle when said nozzle is extended to the use position.

4. The disposable device of claim 3 wherein said second valve means includes a ball valve surface on said sleeve valve body through which said valve body passageway opens, a ball seatable on said ball valve surface, and means for retaining said ball on said ball valve surface until said sleeve body is moved by said abutments and said container is collapsed to apply a predetermined pressure to the fluid contained therein.

5. The disposable device of claim 4 wherein said retaining means includes at least two spaced apart and extending fingers on said sleeve valve body adjacent said ball valve surface and oriented to extend along the passageway in said nozzle, said fingers having inner portions forming a diameter smaller than the outside diameter of said ball to retain said ball on the ball valve surface and wherein said nozzle passageway includes a tapered section engageable with an outer surface on said fingers when the valve sleeve body is in the closed position to deflect the fingers around said ball to force the ball against the ball valve surface until the nozzle is extended to the use position.

6. The disposable device of claim 5 wherein said container includes a bellows portion to permit the nozzle to be moved relative to the container thereby permitting the user to orient the nozzle in the most convenient orientation relative to said container.

7. A disposable device for dispensing douche liquids and the like contained therein, said disposable device comprising a collapsible container having liquid contents, a nozzle telescopically mounted on said container and having a passageway communicating with the interior of said container for dispensing the liquid contents of said container, a portion of said nozzle being retractable into the interior of said container to a storage position and being extendable to a use position, said nozzle passageway having a length thereof by a cylindrical wall portion in the inner end of the nozzle, a sleeve valve mounted in the inner end of said nozzle for controlling the flow of liquids from said container through said nozzle, said sleeve valve including a cylindrical valve body insertable in said cylindrical wall portion of said passageway and dimensioned to sealingly engage with the cylindrical wall portion, said cylindrical valve body having a flow passageway communicating through one end thereof with the passageway in said nozzle, said valve body having a valve port extending radially therethrough communicating with the valve body flow passageway at the inner end thereof and being selectively communicable with the interior of said container, and an abutment flange on said cylindrical valve body and an abutment on said container including a cylindrical abutment skirt mounted on said container in surrounding relation to a portion of said nozzle extending into said container and engageable with said abutment flange on said cylindrical valve body to move said cylindrical valve body relative to said nozzle and cause said valve port in said cylindrical valve body to communicate the interior of said container with said nozzle when said nozzle is extended to the use position.

8. The disposable device of claim 7 additionally including a ball valve means mounted on said nozzle for preventing the flow of fluid through said nozzle passageway when said sleeve valve is open until said container is collapsed by the user to create a predetermined pressure on the fluid contained therein whereby said ball valve means permits the flow of liquid through said nozzle passageway.

9. The disposable device of claim 8 wherein said ball valve means includes a ball valve surface on said sleeve valve body through which said valve body passageway opens, a ball seatable on said ball valve surface, and means for retaining said ball on said ball valve surface until said sleeve body is moved by said abutments and said container is collapsed to apply a predetermined pressure to the fluid contained therein.

10. The disposable device of claim 9 wherein said container includes a bellows portion to permit the nozzle to be moved relative to the container thereby permitting the user to orient the nozzle to the most convenient position relative to said container.

11. The disposable device of claim 9 wherein said retaining means includes at least two spaced apart and extending fingers on said sleeve valve body adjacent said ball valve surface and oriented to extend along the passageway in said nozzle, said fingers having inner portions of diameter smaller than the outside diameter of said ball to retain said ball on the ball valve surface and wherein said nozzle passageway includes a tapered section engageable with an outer surface on said fingers when the valve sleeve body is in the closed position to deflect the fingers around the ball to force the ball against the ball valve surface until the nozzle is extended to the use position.

12. The disposable device of claim 11 wherein the container includes a bellows portion to permit the nozzle to be moved relative to the container thereby permitting the user to orient the nozzle to the most convenient position relative to said container.

13. The disposable device of claim 11 wherein said container has a threaded inlet and said sealing means between said nozzle and said container includes a cap threadably engageable with said threaded inlet, said cap having a circumferentially sealing ridge thereon yieldingly engageable with a circumferential portion of said inlet to provide a fluid tight seal between said cap and said container when said cap is threadably engaged with said threaded inlet, said cap having an opening therethrough with said nozzle extending through said opening, said abutment skirt mounted on said cap and surrounding said opening, said cap having an inwardly directed bead wiper in said cap opening to yieldingly engage a circumferential surface on said nozzle to provide a fluid-tight seal between said cap and said nozzle in the various positions of the nozzle.

14. The disposable device of claim 7 additionally including a threaded inlet on said container and having a circumferential portion, a cap threadably engageable with said threaded inlet, said cap having a circumferentially sealing ridge thereon yieldingly engageable with the circumferential portion of said inlet to provide a fluid tight seal between said cap and said container when said cap is threadably engaged with said threaded inlet, said cap having an opening therethrough with said nozzle extending through said opening, said abutment skirt mounted on said cap and surrounding said opening, said cap having an inwardly directed bead wiper in said cap opening to yieldingly engage a circumferential surface on said nozzle to provide a fluid-tight seal between said cap and said nozzle in the various positions of the nozzle.

15. The disposable device of claim 14 wherein said sleeve valve body includes a ball valve surface on said sleeve valve body at a location near the innermost extent of said sleeve valve body in said nozzle, said valve body passageway extending through and being encircled by said ball valve surface, a ball seatable on said ball valve surface, and means for retaining said ball on said ball valve surface until said sleeve body is moved by said abutments and said container is collapsed to apply a predetermined pressure to the fluid contained therein.

16. The disposable device of claim 15 wherein said retaining means includes at least two spaced apart and extending fingers on said sleeve valve body adjacent said ball valve surface and oriented to extend along the passageway in said nozzle, said fingers having inner portions of diameter smaller than the outside diameter of said ball to retain said ball on the ball valve surface and wherein said nozzle passageway includes a tapered section engageable with an outer surface on said fingers when the valve sleeve body is in the closed position to deflect the fingers around the ball to force the ball against the ball valve surface until the nozzle is extended to the use position.

17. The disposable device of claim 15 wherein said container includes a bellows portion to permit the nozzle to be moved relative to the container thereby permitting the user to orient the nozzle to the most convenient position relative to said container.

18. A disposable douche comprising a collapsible container, a nozzle telescopically mounted on said container and having a passageway with an inner end and an outer end, said inner end communicating with the interior of said container for receiving liquid from the container and dispensing the liquid outwardly through opening in said outer end, a portion of said nozzle being retractable into the interior of said container to a storage position and being extendable to a use position, a first valve means movably mounted on said nozzle for controlling the flow of liquids from said container through said nozzle, means for opening said first valve means in response to movement of said nozzle to said use position, said container having a threaded inlet and sealing means between said nozzle and said container including a cap threadably engageable with said threaded inlet, said cap having a circumferentially sealing ridge thereon yieldingly engageable with a circumferential portion of said inlet to provide a fluid tight seal between said cap and said container when said cap is threadably engaged with said threaded inlet, said cap having an opening therethrough with said nozzle extending through said opening, said cap having an inwardly directed sealing bead wiper in said cap opening to yieldingly engage a circumferential surface on said nozzle to provide a fluid-tight seal between said cap, and said nozzle in the various positions of the nozzle, and a second valve means mounted on said nozzle for preventing the flow of fluid through said nozzle passageway when said first valve means is open until said container is collapsed by the user to create a predetermined pressure on the fluid contained therein whereby said second valve means permits the flow of liquid through said passageway, wherein said second valve means includes a ball valve surface on said sleeve valve body through which said valve body passageway opens, a ball seatable on said ball valve surface, and means for retaning said ball on said ball valve surface until said sleeve body is moved by said abutments and said container is collapsed to apply pressure to the liquid contained therein.

19. The disposable device of claim 18 wherein said retaining means includes at least two spaced apart and extending fingers on said sleeve valve body adjacent said ball valve surface and oriented to extend along the passageway in said nozzle, said fingers having inner portions of diameter smaller than the outside diameter of said ball to retain said ball on the ball valve surface and wherein said nozzle passageway includes a tapered section engageable with an outer surface on said fingers when the valve sleeve body is in the closed position to deflect the fingers around the ball to force the ball against the ball valve surface until the nozzle is extended to the use position.

* * * * *